United States Patent [19]

Duggins

[11] Patent Number: 4,735,726

[45] Date of Patent: Apr. 5, 1988

[54] PLASMAPHERESIS BY RECIPROCATORY PULSATILE FILTRATION

[75] Inventor: Ray B. Duggins, Chadds Ford, Pa.

[73] Assignee: E. I. Du Pont de Nemours and Company, Wilmington, Del.

[21] Appl. No.: 9,003

[22] Filed: Jan. 28, 1987

Related U.S. Application Data

[63] Continuation-in-part of Ser. No. 478,812, Mar. 30, 1983, abandoned, which is a continuation-in-part of Ser. No. 349,371, Feb. 16, 1982, abandoned, which is a continuation-in-part of Ser. No. 287,116, Jul. 22, 1981, abandoned.

[51] Int. Cl.$^4$ .............................................. B01D 13/00
[52] U.S. Cl. ..................... 210/637; 210/651; 210/321.75; 210/371.84
[58] Field of Search ............... 210/636, 637, 649, 650, 210/651, 652, 653, 654, 655, 321.1, 321.2, 321.3, 321.4, 321.5, 416.1–416.5, 433.1, 433.2

[56] References Cited

U.S. PATENT DOCUMENTS

| | | |
|---|---|---|
| 3,077,268 | 2/1963 | Gobel et al. .................... 210/321.4 |
| 3,211,645 | 10/1965 | Ferrari ................................ 210/637 |
| 3,212,642 | 10/1965 | Kylstra ................................ 210/321 |
| 3,354,618 | 11/1967 | Dounoucos ........................... 55/158 |
| 3,429,757 | 2/1969 | Nash ..................................... 156/70 |
| 3,541,005 | 11/1970 | Strathmann et al. ................ 210/636 |
| 3,684,097 | 8/1972 | Mathewson, Jr. et al. ......... 210/321 |
| 3,705,100 | 12/1972 | Blatt et al. .......................... 210/927 |
| 3,738,495 | 6/1973 | Esmond ............................ 210/321.3 |
| 3,853,756 | 12/1974 | Stana ............................. 210/433.2 X |
| 3,966,616 | 6/1976 | Bray .................................. 210/433.2 |
| 4,001,117 | 1/1977 | Trechsel ............................... 210/180 |
| 4,075,091 | 2/1978 | Bellhouse ............................ 210/637 |
| 4,191,182 | 3/1980 | Popovich et al. .................. 128/214 R |
| 4,212,742 | 7/1980 | Solomon et al. ..................... 210/247 |
| 4,213,858 | 7/1980 | Boberg et al. ................. 210/497.1 X |
| 4,343,705 | 8/1982 | Legg .............................. 210/445 X |

FOREIGN PATENT DOCUMENTS

| | | | |
|---|---|---|---|
| 2653875 | 6/1978 | Fed. Rep. of Germany ... | 210/433.2 |
| 2925143 | 1/1981 | Fed. Rep. of Germany ... | 210/433.2 |
| 167009 | 12/1980 | Japan .................................. | 210/321.2 |
| 01043 | 5/1980 | PCT Int'l Appl. ................. | 210/321.2 |
| 1381410 | 1/1975 | United Kingdom ............... | 210/636 |
| 1555389 | 11/1979 | United Kingdom ............. | 210/433.2 |
| 2037614 | 7/1980 | United Kingdom ............. | 210/433.2 |
| 2048114A | 12/1980 | United Kingdom ............. | 210/321.2 |

OTHER PUBLICATIONS

Strathmann, H., *Journal of Membrane Science*, 9 (1981), pp. 121–189.
Dorson et al., Chem. Eng. Prog. Symp. Ser. 64, 1968, pp. 85–89 "A Pulsating Ultrafiltration Artificial Kidney".
Driscoll et al., Trans. Amer. Soc. Artif. Int. Organs XXIII, 1977, pp. 470–478.
Bixler et al., Trans. Amer. Soc. Artif. Int. Organs XIV, 1968, pp. 99–108.

*Primary Examiner*—David Sadowski

[57] ABSTRACT

A process for continuous plasmapheresis, which process comprises conducting blood over a microporous membrane in reciprocatory pulsatile flow, and preferably further comprises reducing the transmembrane pressure difference to below zero during each forward and reverse flow. Apparatus for carrying out the process are also disclosed.

36 Claims, 2 Drawing Sheets

PLASMAPHERESIS BY RECIPROCATORY PULSATILE FILTRATION

Cross Reference to Related Application

This application is a continuation-in-part of application Ser. No. 478,812, filed Mar. 30, 1983, which is a continuation-in-part of application Ser. No. 349,371, filed Feb. 16, 1982, which is a continuation-in-part of application Ser. No. 287,116, filed July 22, 1981, all prior applications having been expressly abandoned.

TECHNICAL FIELD

This invention pertains to a process and an apparatus for plasmapheresis by reciprocatory pulsatile filtration with microporous membranes.

BACKGROUND INFORMATION

Plasmapheresis is a process of separating plasma from whole blood. The plasma-depleted blood is comprised principally of cellular components, e.g., red blood cells, white blood cells and platelets. Plasma is comprised largely of water, but also contains proteins and various other noncellular compounds, both organic and inorganic.

Continuous plasmapheresis is the process of continuously separating plasma from whole blood.

Plasmapheresis is currently used to obtain plasma for various transfusion needs, e.g., preparation of fresh-frozen plasma, for subsequent fractionation to obtain specific proteins such as serum albumin, to produce cell culture media, and for disease therapies involving either the replacement of plasma or removal of specific disease-contributing factors from the plasma.

Plasmapheresis can be carried out by centrifugation or by filtration. Generally, in known filtration apparatus, whole blood is conducted in a laminar flow path across one surface, i.e., the blood side surface, of a microporous membrane. Useful microporous membranes have pores which substantially retain the cellular components of blood but allow plasma to pass through. Such pores are referred to herein as cell-retaining pores. Typically, cell-retaining pore diameters are 0.1 $\mu$m to 1.0 $\mu$m.

In such known apparatus, as the blood flows through the flow path, the cellular components tend to migrate towards the center or axis of the path. Ideally, plasma occupies the periphery of the path so that it is predominantly plasma that contacts the membrane. A pressure difference across the membrane causes some of the plasma to pass through the pores of the membrane while plasma-depleted blood continues to flow to the end of the path. Ideally, the filtrate is cell free; the plasma-depleted blood collected at the end of the flow path is concentrated, i.e., is depleted in plasma and therefore has an increased hematocrit (volume percent of red blood cells).

After blood has been conducted across the surface of a membrane at normal venous flow rates for some time, the transmembrane flow of plasma becomes impaired. This phenomenon is herein sometimes referred to as membrane fouling or simply as fouling. Known techniques for reducing fouling, i.e., increasing the length of time for which the process can be carried out without the occurrence of significant impairment of plasma flow, include varying the flow path size so as to optimize the wall shear rate along the length of the flow path as disclosed in U.S. Pat. 4,212,742, and recycling a portion of the plasma-depleted blood to increase the velocity of blood in the flow path; the latter technique may result in less plasma-depletion.

Various filtration devices for plasmapheresis are disclosed in the literature. U.S. Pat. No. 3,705,100 discloses a center-fed circular membrane having a spiral flow path. U.S. Pat. No. 4,212,742 discloses a device having divergent flow channels. German Pat. No. 2,925,143 discloses a filtration apparatus having parallel blood flow paths on one side of a membrane and parallel plasma flow paths, which are perpendicular to the blood flow paths, on the opposite surface of the membrane U.K. Patent Application No. 2,037,614 discloses a rectilinear double-membrane envelope in which the membranes are sealed together at the ends of the blood flow path. U.K. Patent Specification No. 1,555,389 discloses a circular, center-fed, double-membrane envelope in which the membranes are sealed around their peripheries. German Pat. No. 2,653,875 discloses a circular, center-fed double-membrane device in which blood flows through slot-shaped filter chambers It is an object of this invention to provide a process and apparatus for plasmapheresis by filtration. It is a further object to provide such a process and apparatus whereby highly concentrated, plasma-depleted blood can be continuously collected without significant hemolysis and with reduced membrane fouling.

DISCLOSURE OF THE INVENTION

For further comprehension of the invention and of the objects and advantages thereof, reference may be made to the following description and to the appended claims in which various novel features of the invention are more particularly set forth.

The invention herein resides in process and apparatus for carrying out a plasmapheresis and is such that plasma is collected at the rate of at least about 0.01 mL/min/cm$^2$ of microporous membrane and the resultant plasma-depleted blood exhibits a hematocrit of at least about 60%.

It has been found that the above objects can be achieved by conducting blood over the surface of a membrane in reciprocatory pulsatile flow. In particular, the invention resides in a method for continuously separating plasma from blood, which method comprises:

(1) conducting blood in a forward direction over a first surface, i.e., a blood side surface, of each of one or more membranes having cell-retaining pores, while maintaining a net positive transmembrane pressure difference;

(2) terminating the forward conducting of blood over the first surface of the membrane;

(3) conducting the blood in the reverse direction over said first surface, the volume of blood flowed in the reverse direction being less than the volume of blood flowed in the forward direction in step (1);

(4) repeating steps (1)–(3) in sequence and collecting plasma which passes through each membrane from a second surface, i.e., a plasma side surface, thereof and collecting plasma-depleted blood from said first surface.

Still more specifically, the invention resides in an improved method for plasmapheresis wherein whole blood is introduced and conducted in a forward direction from an upstream area of a first surface of each of one or more membranes having cell-retaining pores to a downstream area of the first surface, plasma-deplated blood is collected from the downstream area of the first surface, and plasma is separately collected from a second surface of each of the one or more membranes, in a system closed off from the atmosphere, comprising:

(a) while maintaining a net positive transmembrane pressure difference across the membrane, conducting plasma-depleted blood in the reverse direction over the first surface by delivering collected plasma-depleted blood to the downstream area of the first surface and reducing the transmembrane pressure difference across the membrane in the upstream area whereat whole blood is introduced to about $\leqq 0$ by either withdrawing and collecting blood from the upstream area of the first surface or increasing the pressure on a second surface of the one or more membranes, while collecting blood from the upstream area of the first surface, so that blood in the upstream area of the first surface is at a pressure which is lower than the downstream plasma-depleted blood pressure;

(b) terminating the reverse conducting of step (a);

(c) while maintaining the net positive transmembrane pressure difference across the membrane, conducting whole blood in the forward direction over the first surface by delivering collected blood from step (a) to the upstream area of the first surface and reducing the transmembrane pressure difference across the membrane in the downstream area whereat plasma-depleted blood is collected to about $\leqq 0$ by either withdrawing and collecting plasma-depleted blood from the downstream area of the first surface or increasing the pressure on a second surface of the one or more membranes, while collecting plasma-depleted blood from the downstream area of the first surface, so that plasma-depletd blood in the downstream area of the first surface is at a pressure which is lower than the upstream blood pressure;

(d) repeating steps (a) to (c) in sequence; and (e) collecting plasma at the rate of at least about 0.01 mL/min/cm$^2$ of membrane and plasma-depleted blood having a hematocrit of at least about 60%.

The invention further resides in said process wherein the transmembrane pressure difference is reduced during periods of flow, preferably to below zero.

The invention also resides in apparatus for carrying out the aforesaid steps. In particular, the invention also resides in apparatus for separating plasma from blood which apparatus comprises one or more membranes having cell-retaining pores, means for conducting blood forward at a net positive transmembrane pressure difference and reverse over a first surface of each membrane, means for reducing the transmembrane pressure difference during the forward and reverse conducting of blood, means for collecting plasma which passes through each membrane from a second surface thereof, means for withdrawing and collecting blood from said first surface, means for withdrawing and collecting plasma-depleted blood from said first surface, means for delivering collected blood to said first surface, means for delivering collected plasma-depleted blood to said first surface and means for operating the apparatus closed off from the atmosphere. The invention also resides in said apparatus comprising means for reducing the transmembrane pressure difference during periods of flow, preferably, to below zero.

Further, the invention resides in the membrane filter module which comprises:

first and second opposing module housing plates having circular recesses within opposing surfaces so as to form a blood flow region between two plasma flow regions, there being a central blood inlet port connected to the blood flow region; a blood collection channel, around the blood flow region, connected to a plasma-depleted blood outlet port; and a plasma collection channel around each plasma flow region connected to a plasma outlet port;

a plasma-side support within each plasma flow region; and a pair of membranes, having cell-retaining pores, between each plasma flow region and the blood flow region, there being an elastomeric seal between each membrane and each plate and a blood flow path between the membranes.

means for conducting blood forward at a net positive transmembrane pressure difference and reverse over a first surface of each membrane;

means for reducing the transmembrane pressure difference during the forward and reverse conducting of blood;

means for collecting plasma which passes through each membrane from a second surface thereof;

means for withdrawing and collecting blood from the blood flow region;

means for delivering collected blood to the blood flow region;

means for withdrawing and collecting plasma-depleted blood from the blood flow region;

means for delivering plasma-depleted blood to the blood flow region; and means for operating the module closed off from the atmosphere.

The invention also resides in such a filtration module in which blood side supports are located between the membranes. Such module may have means for imparting reciprocatory pulsatile flow to blood in the flow path connected thereto.

By comprises is meant that the invention includes the aforesaid steps and elements although it is to be understood that other steps and elements are not excluded from the invention, e.g., recycling the plasma-depleted blood, treating plasma during filtration, diluting the blood with a compatible fluid and measuring various biologically significant factors and means therefor.

In the following description and examples of the invention, the term "forward" is used to indicate a direction generally away from the source of blood; reverse indicates a direction generally towards the source of blood. Transmembrane pressure difference is determined by subtracting the pressure on the plasma side, i.e., the second surface of the membrane, from the pressure on the blood side, i.e., the first surface of the membrane. It is to be understood that the transmission pressure varies across the membrane with the distance the blood has traveled from the source. Thus, with regard to this invention, since localized transmembrane pressure differences across the membrane may be either positive or negative, only the system transmembrane pressure differences are reported, being referred to herein as net transmembrane pressure differences. The term "fouling" is used to describe the impairment of plasma flow through a membrane.

In the invention, blood may be conducted in a forward direction in a flow path over the first surface of a membrane by any means which does not cause significant damage to cellular components, which does not cause significant discomfort or danger to a donor or patient, which provides sufficient forward flow rate and pressure to efficiently fractionate blood in the manner and under the conditions described below, and which allows the forward flow to be periodically interrupted as described below. Examples include various pumps such as a rotary peristaltic pump, a piston or syringe pump, and a plunger or hose pump; even manually operated devices such as a flexible blood-containing chamber which can conduct blood forward when compressed may be used.

The membrane is made of any blood-compatible material, and has cell-retaining pores, i.e., pores which substantially retain cellular components but allow plasma to pass through; such pores are typically about 0.1 to 1.0 μm average diameter. The selection of a pore size may vary with the goal of a particular treatment. Useful membranes are described in some of the above-cited references relating to plasmapheresis. The membrane may be of any suitable shape, e.g., tubular, such as hollow fibers or any planar shape. When planar membranes are used, membranes having low elongation, e.g., less than about 65%, high modulus, e.g., at least about 10 kpsi (70 MPa), and high tensile strength, e.g., at least about 3000 psi (20 MPa), when tested wet in accordance with standard procedures, are preferred, because they are dimensionally stable. As exemplary of membranes having these preferred properties are mentioned the HT 450 polysulfone membrane commercially available from Gelman Sciences, Inc. and the polyester and polycarbonate membranes commercially available from Nuclepore Corporation. Of these, thin, e.g., less than about 1 mil (25 μm), preferably less than 0.5 mil (13 μm), smooth polycarbonate or polyester capillary pore membranes are preferred because, in laboratory experiments, such membranes were found, in general, to perform better than the tortuous path membranes which were tested. Under various conditions of practice, however, any of the above-described or other types of membranes may prove to be more or less advantageous. It is to be understood that more than one membrane in any arrangement may be used. Conveniently, several membranes are stacked within an enclosed module so that blood is fractionated by more than one membrane simultaneously. A planar membrane is preferably supported on the plasma side and more preferably on both sides by, e.g., supports comprising plates having grooves, pores or projections or fabric-like materials. A preferred plasma side support comprises a plurality of layers of a nonwoven polyester fabric.

From the location at which the blood first contacts the membrane, which may or may not be near a point on an edge or end of the membrane, blood is conducted in a forward direction in one or more flow paths. A flow path is the space through which the blood flows on the first surface of the membrane. For example, in a preferred embodiment, the membrane is planar and circular, the location at which the blood contacts the membrane is near the center thereof, and the flow path extends radially, ending near the periphery of the membrane. It is apparent that when the membrane is tubular and blood is conducted within the tube, the membrane may alone define the flow path. Typically the depth of blood in each flow path is less than about 30 mils (0.76 mm). Preferably, said depth is also at least about 4 mils (0.10 mm) but, preferably no more than about 10 mils (0.25 mm).

The rate at which blood is conducted over the first surface of the membrane is at least as high as may be needed to provide a net positive transmembrane pressure difference. The flow velocity typically varies during each period of forward flow. The preferred average forward flow rate from the source to the membrane is about 50 to 60 ml-min$^{-1}$ when the source of blood is a vein of a normal human donor although the process may be carried out at higher or lower flow rates.

Plasma is driven through the cell-retaining pores in the membrane at a practical rate by a positive transmembrane pressure difference. Typically, positive transmembrane pressure difference is generated primarily by resistance to forward flow, but it can also be generated in other ways, e.g., by decreasing pressure on the plasma on the second surface.

It has been found that the amount of transmembrane pressure difference that can be withstood by blood without hemolysis is largely a function of cell-retaining pore size. For most purposes, the preferred pore diameter is about 0.4 to 0.5 μm. In this range, a positive transmembrane pressure difference of up to about 4 psi (28 kPa) is desirable although up to about 1.5 psi (10 kPa) is believed to be preferred. When the pore diameter is smaller or larger, higher or lower transmembrane pressure differences, respectively, are acceptable. It is to be understood that the pressure on the blood side and the plasma side surfaces, and the transmembrane pressure difference, may vary during the course of a treatment and in different regions of the flow path.

After the conducting of blood over the first surface of the membrane with a positive transmembrane pressure difference is continued for some time, the membrane becomes progressively fouled, i.e., the flow of plasma through the membrane becomes increasingly impaired. The length of time for which blood can be so conducted is believed to depend upon several factors such as, e.g., flow velocity, hematocrit, pore size, transmembrane pressure difference, and the individual characteristics of the blood being treated. The frequency and volume of the reciprocatory pulses are selected to maximize the flow of plasma through the membrane without causing extensive blood trauma. In planar blood flow paths having a height of about 4 to 10 mils (100 to 254 μm), a useful frequency and volume are about 20 to 140 pulsations per minute, preferably 40 to 80 pulsations per minute, 0.5 to 4 mL per pulsation, preferably abut 3 mL. By pulsations per minute, also referred to herein as cycles per minute, is meant the number of times per minute the blood is conducted through a cycle, a cycle consisting of one forward movement and one reverse (backward) movement of blood acorss the membrane. Said parameters should be selected to provide a mean linear velocity up to about 400 mm-sec$^{-1}$, preferably, up to about 250 mm-sec$^{-1}$. These parameters may be adjusted during a particular treatment, but conveniently may be selected and fixed for an entire treatment.

After the forward conducting of blood is terminated, blood is conducted in the reverse direction in each flow path. The termination of forward flow and the conducting of blood in the reverse direction need not occur simultaneously over the entire membrane. Because blood is conducted in forward and reverse directions with a net forward flow during the procedure, the blood flow is referred to as reciprocatory pulsatile flow.

In a preferred embodiment, the transmembrane pressure difference is reduced when conducting blood in either direction. The preferred method is by using a pulse pump connected to the module blood inlet and outlet. The pulse pump suction produces a negative pressure at peak flow rate over the portion of the filtration membrane from which pulse blood is being drawn for that portion of the pulse cycle. Another method is to increase plasma side pressure so that the blood in the down stream area of the membrane can be at pressure which is positive but lower than the upstream blood pressure and lower than the plasma side pressure. Other means will become apparent hereinafter. It is to be understood that said reduction need not occur simultaneously over the entire membrane, e.g., at any given instant, there may be areas on the membrane with high transmembrane pressure difference and other areas with low transmembrane pressure difference and, at any given point on the membrane, the transmembrane pressure difference may continuously fluctuate. Preferably, the transmembrane pressure difference is reduced to below zero, e.g., about −0.1 to −3.0 psi (−0.7 to −20.7 kPa), and, more preferably, to about −0.8 to −1.0 psi (−5.3 to −6.9 kPa). Preferably, a large amount of plasma backflow through the membrane is avoided.

The duration of the reverse flow of blood is selected to maintain substantially unimpaired flow of plasma through the membrane as well as to increase the distance which the blood travels across the membrane. A wide range of reverse flow durations are useful. The volume of blood flowed in the reverse direction is less than the volume of blood flowed forward.

It is to be understood that reverse flows of blood may begin in some regions of the flow paths prior to cessation of the forward flow of blood in other, or even in the same, regions, i.e., forward and reverse flows may overlap. It is preferred that the frequency of the reciprocatory pulsations be low, but at least twenty, in the early stages of a treatment and then be gradually raised to a desirable frequency. It may be necessary to adjust the apparatus during a procedure to maintain desirable pressures and flows.

The blood which approaches the ends of each flow path is plasma-depleted blood. It is collected and conducted away from the membrane by any suitable means, as is the plasma which flows through the membrane.

The reciprocatory pulsations and transmembrane pressure difference reductions, as is apparent from the above discussion, can be carried out in numerous ways. Typically, the means include a plurality of coordinated pumps and valves positioned on blood, plasma-depleted blood and/or plasma lines. Pressure accumulators, or surge chambers, may also be useful. Some such useful means are disclosed in the following examples, which are illustrative only, of treatments in accordance with the invention. Other means will be obvious to persons skilled in the art.

Figure 1:
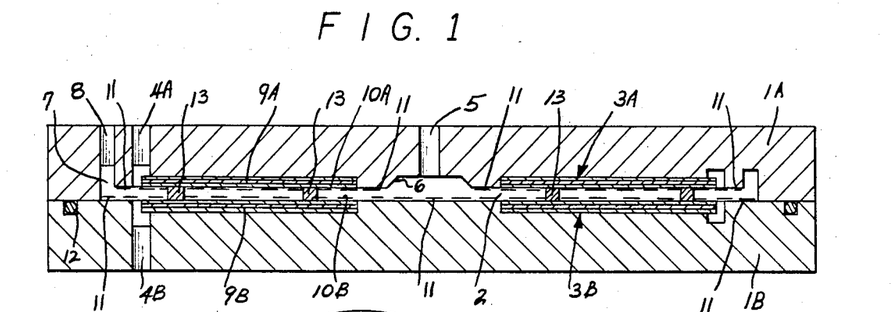
FIG. 1 is a cross-section of a double-membrane filtration module which may be used in the process of the invention, taken along line I—I of FIG. 2.

Referring to FIG. 1, a filtration module, which may be used with reciprocatory pulsatile flow and may have means for generating reciprocatory pulsations connected thereto, comprises two circular opposing module housing plates 1A, 1B which are prepared from a blood-compatible material. A circular blood flow region 2 is recessed within an opposing surface of one or both plates. Further recessed within each plate is a plasma flow region 3A, 3B. Typically, though not necessarily, the plasma flow region is of smaller diameter than the blood flow region.

The depth of the plasma flow region is typically about 5 to 20 mils (127 to 508 μm). The surface of the plasma flow region may be smooth or grooved to enhance radial flow of plasma. In the plasma flow region, or connected thereto, may be means for treating the plasma for the removal of disease-contributing factors.

One or both plates 1A, 1B have plasma outlet ports 4A, 4B connected to the plasma flow regions 3A, 3B via a plasma collection channel around the plasma flow regions, e.g., about 3 mm deep and 1.5 mm wide. There may be one or more of such ports in either or both plates. The ports and channel may be located at any position but preferably, as herein illustrated, are located near the periphery of each plasma flow region.

Near the center of plate 1A is blood inlet port 5, the walls 6 of which extend through plasma flow region 3A to the blood flow region 2. Around the periphery of blood flow region 2 is a plasma-depleted blood collection channel 7. This channel connects to one or more plasma-depleted blood outlet ports 8.

Within each plasma flow region is a plasma side membrane support 9A, 9B which may be, e.g., a plate having grooves, pores or projections or fabric-like materials. As illustrated, the plasma side supports are comprised of layers of fabric-like materials, such as layers of a nonwoven polyester fabric. The preferred support is three layers of 4 mil (102 μm) thick Hollytex, made by calendering Du Pont Reemay ® spunbonded polyester, because it provides adequate support while allowing transverse and radial flow of plasma. The support 9A which fits in plasma flow region 3A is provided with an aperture which fits around wall 6 of blood inlet port 5.

Within each blood flow region is a membrane 10A, 10B. Membrane 10A which fits in blood flow region 2 in plate 1A is provided with an aperture which lies approximately in registry with blood inlet port 5.

The membranes 10A, 10B are adhered to the plates near the peripheral edges of the membranes and, in the case of the membrane 10A, near the edge of the aperture in the membrane which is in registry with blood inlet port 5, with an elastomeric adhesive. Use of an elastomeric seal provides sufficient flexibility to avoid rupture of the membranes during use. The areas of membranes 10A, 10B which are adhered to plates 1A, 1B are identified in FIG. 1 by the number 11.

It has been found that when thin polycarbonate or polyester membranes which have low break elongation, i.e., less than about 40%, are employed in filter modules in which, as herein illustrated, the membranes are not rigidly supported across a large part of their surface areas, it is advantageous to employ an elastomeric seal between the membranes and supports. Use of an elastomeric seal provides sufficient flexibility to avoid rupture of the membranes during use. When such membranes are employed, the seal preferably has a break elongation of at least about 100%. The optimal break elongation will depend on several factors which will be obvious to persons skilled in the art, including the thickness of the seal. An elastomeric seal which has been found to perform well with such membranes is an adhesive having a break elongation of about 400% and applied in a layer about 3 mils (76 μm) thick.

When the module is assembled, the corresponding flow regions of each plate are adjacent. The plates are held together by any suitable means, e.g., clamps, bolts and adhesives. An O-ring 12 can be used to seal the plates. The region between the membranes is the blood flow path. The total effective surface area of the membranes, i.e., the sum of the areas on both membranes through which plasma can flow, is about 0.02 to 0.06 m².

Blood side supports 13 are located between the membranes. Blood side supports, though not necessary, have been found to be advantageous when nonrigid plasma side supports, such as layers of Hollytex, which may tend to buckle during use, are employed. Various suitable supports are described in the literature. The illustrated and preferred supports comprise a plurality of smooth pillars, e.g., substantially circular, dots of cured adhesive of the type used to adhere the membranes to the plates. These have sufficient softness to avoid breakage of the membranes during use.

Figure 2:
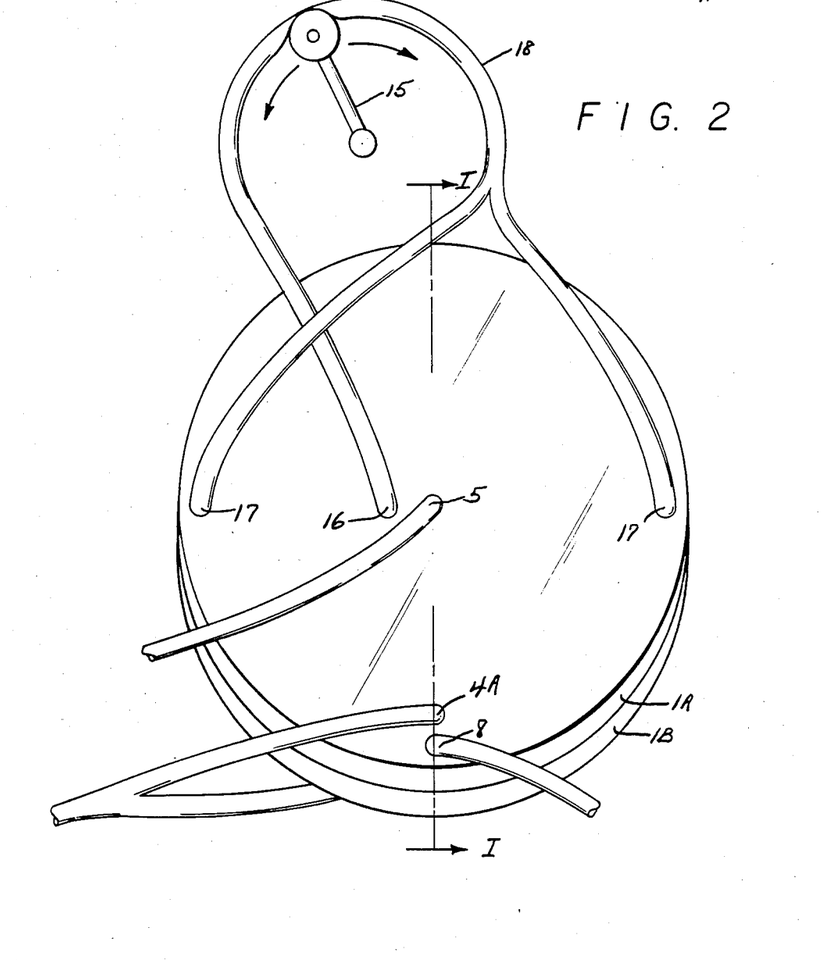
FIG. 2 is a perspective view of an illustrative embodiment of the filtration module of FIG. 1 having a loop and an oscillator to oscillate blood in a blood flow path between inlet and outlet.

FIG. 2 is an illustration of an embodiment of the invention in which the filtration module of FIG. 1 is used. The loop for generating reciprocatory pulsations as illustrated herein is the invention of one other than the inventor herein. Blood is conducted from the source to the blood flow path via blood inlet port 5 in module housing plate 1A. Plasma which passes through the membranes exits from the module through a plasma outlet port 4A, and a second plasma outlet port, not shown. Plasma-depleted blood from the end of the blood flow path exits from the module through plasma-depleted blood outlet port 8. In addition, blood flow is pulsed in reciprocatory fashion by a peristaltic oscillator 15, which is connected to central and peripheral ports 16 and 17 through loop 18, which peripheral ports are connected to areas near an end of the flow path, directly, or indirectly via a blood collection channel, not shown. The loop is preferably short so that blood in the loop is frequently mixed and exchanged with blood in the flow path. There preferably is little or no exchange of blood across the oscillator. Any suitable type of pump may be used to cause the reciprocatory pulsations. Such pumps are described in the literature and in the Examples below; a peristaltic pump is preferred. Preferably, though not necessarily, the oscillator is connected to the blood flow path via one centrally located port and two peripherally located ports, as shown, or to the blood inlet and plasma-depleted blood outlet lines at a location close to the module. The duration and frequency of oscillations can be regulated by adjusting the oscillator. The forward and reverse strokes are typically of equal volume.

Figure 3:
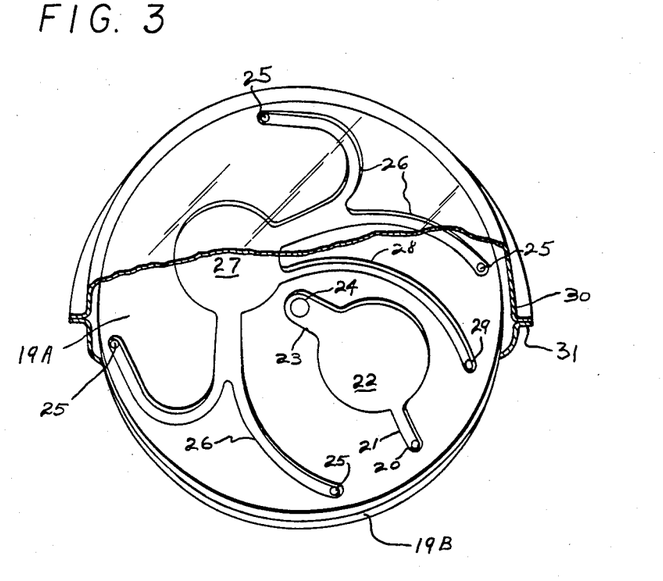
FIG. 3 is a perspective view of a module having an end plate which has reciprocatory pulse cavities.

FIG. 3 illustrates a module having an end plate, i.e., module housing plate, which has reciprocatory pulse cavities integral therewith. The end plate is the invention of one other than the inventor herein.

Blood is conducted into the module via an inlet, not shown, in end plate 19B and is conducted through a matched port 20 in end plate 19A. From port 20 in end plate 19A, the blood is conducted through shallow channel 21, 0.2 inch (5.1 mm) wide × 0.06 inch (1.5 mm) deep, into inlet reciprocatory pulse cavity 22 which has a volume of about 3 mL and is about 2 inches (50.8 mm) in diameter × 0.06 inch (1.5 mm) deep. Cavity 22 is employed in the generation of reciprocatory pulsations as described below. From cavity 22, the blood is conducted through shallow channel 23, 0.5 inch (127 mm) wide × 0.13 inch (3.3 mm) deep, to blood flow path inlet 24 which is about 0.38 inch (9.7 mm) in diameter. The blood is conducted through port 24 into a blood flow region between two membranes as described above. Plasma-depleted blood is conducted through flow path outlets 25 and through branch channels 26 to outlet reciprocatory pulse cavity 27 in end plate 19A. The branch channels from the four outlets 25, which are equidistant from each other, begin as four channels each about 0.250 inch (6.4 mm) wide × 0.060 inch (1.5 mm) deep and merge into two channels each about 0.500 inch (12.7 mm) wide × 0.060 inch (1.5 mm) deep. The branch channels are of equal length and cross-section so as to produce substantially equal pressure conditions during use. Cavity 27 is also employed in the generation of reciprocatory pulsations as described below. From cavity 27, the plasma-depleted blood is conducted through shallow channel 28, 0.200 inch (5.1 mm) wide × 0.060 inch (1.5 mm) deep, and through plasma depleted blood outlet 29 which extends through a matched port in end plate 19B.

Plasma which passes through the membranes flows radially in a plasma flow path and through a plasma collection channel, as described above, to an outlet port, not shown, in end plate 19B.

The entire module is enclosed by envelope 30 which is comprised of two sheets of a flexible blood impermeable material, such as poly(vinyl chloride), the sheets being joined together at seal 31 around the perimeter of the stack. The envelope thus provides a unitary flexible enclosure for the module. The three apertures in end plate 19B mate with tube connectors in envelope 30.

Envelope 30 covers and seals the various channels, cavities and apertures in end plate 19A and forms a flexible diaphragm over each cavity 22, 27. A perimeter lip, not shown, around each cavity and channel in end plate 19A aids in sealing. Reciprocatory pulsations are generated by alternately compressing the diaphragm over each cavity 22, 27 such as by the use of reciprocating plungers.

All of the above illustrated modules must be clamped using pressure which is at least sufficient to offset internal pressure. In the examples, below, a series of C-clamps around the perimeter of each module was employed.

EXAMPLES

In all of the following examples, which are illustrative of single pass treatments to separate plasma from blood in accordance with the invention, compatibility-matched human blood collected in either ACD or heparin was used. The hematocrit of the blood, which was maintained at 37° C. during treatment, was 37-38%.

In all Examples, planar circular supported membranes were encased in membrane filter modules made from Du Pont Lucite® acrylic resin. The membrane filter modules each comprised two circular discs between which were placed one or two supported membranes. Blood was fed to an inlet port at the center of the module and conducted radially therefrom across the surface of each membrane. Plasma-depleted blood and plasma were collected by means of peripheral channels, cut into the discs, which led to outlet ports.

The membranes were polycarbonate capillary pore membranes, available from Nuclepore Corporation, having average cell-retaining pore diameters of about 0.4 μm and about 10% pore area and were about 10 μm thick.

Three materials were alternatively used in the construction of membrane supports. One of these was Hollytex and two were high density polyethylene. Hollytex is a nonwoven polyester fabric produced from layers of Du Pont Reemay ® spunbonded polyester by a calendering procedure. The Hollytex material was used in layers 10 mils (254 μm) or 4 mils (102 μm) thick. The polyethylene materials were porous plates about 6.3 mils (160.0 μm) thick; one had pores which were about 70 μm and the other, about 120 μm, in diameter. Radial channels in the disc below the polyethylene plate allowed for lateral flow of plasma.

Prior to each treatment, the module was purged of air by flushing with saline. The Hollytex supports were first solvent-exchanged in isopropanol, soaked in saline and then placed wet in the membrane filter module. The membrane filter module was submerged in saline, 37° C., during treatment to prevent air leakage. Removing air from and maintaining air out of the apparatus is important.

The transmembrane pressure difference was measured by means of pressure strain gauge transducers and monitored near the center and/or near the periphery of the module and was recorded, usually at 5 to 10 min. intervals. The plasma side of the apparatus was vented, except where noted, and was assumed to be at atmospheric pressure.

Hemolysis was determined by visual observation of samples of plasma periodically collected during each treatment.

The operating conditions and results of each example are tabulated after a general description of the apparatus used therein. Elapsed time is in minutes and indicates the times during each treatment when measurements were taken. Peak and low pressures are in psig (kPa) and were measured near the indicated locations. Blood flow rate is the rate of flow of whole blood from the source to the module in mL per min. Plasma flow rate is the flow rate of collected plasma in mL per min. The hematocrit (Hct.) of plasma-depleted blood which was collected was calculated. Flux is mL of plasma collected per min. per cm² of membrane filter.

It will be apparent to one skilled in the art from a reading of this specification, including the examples, that the results achieved depend on a wide variety of factors, including but not limited to the characteristics of the whole blood, the pore size of the microporous membrane, the blood velocity across the membrane, the depth of the blood on the membrane, the frequency of the blood pulsations across the membrane, the transmembrane pressure difference, and the rate of plasma removal. In general, the data provided in the following tables for blood flow rate, hematocrit and plasma flux support the conclusion that as the blood flow rate is increased, the flux is increased but the hematocrit is decreased.

EXAMPLE 1

This example illustrates plasmapheresis by reciprocatory pulsatile filtration using two membranes in a membrane filter module such that blood is filtered by both membranes simultaneously.

Two layers of Hollytex were placed between two membranes so that blood flowed across the first surfaces of both membranes within recessed flow regions cut into the inside surfaces of the discs and plasma which passed through the membranes flowed radially through the support between the membranes. The blood flow paths were about 8 mils (203.2 μm) in depth and had a combined surface area of about 0.05 m². Plasma-depleted blood from the ends of the flow paths was conducted further through outlet ports and collection tubing to a collection vessel.

Blood was conducted forward and reverse by two pumps which were similar to the hose pump described in U.K. Specification No. 2,020,735, published Nov. 21, 1979, except that the outlet valves were removed, and which were positioned between the blood bag and the membrane filter module. Each pump comprised an inlet valve and a 4" (10.2 cm) plunger. The inlet valves were closed while the plungers were rising and were partially closed while the plungers were withdrawing so that blood was conducted from the directions of the blood bag and of the membrane filter module as the plungers were withdrawing. The plungers never completely occluded the tubing. Each pump displaced about 3.2 mL during each forward pulse.

Blood passed from the blood bag through a single tubing which was divided into two lines. Each line passed through one of the pumps and was rejoined into a single line.

Blood was also conducted in the reverse direction by pressure which accumulated in a surge chamber of about 50 mL which was connected by tubing to the blood flow path at two locations near the end of the flow path.

A 0.33 psi (2.3 kPa) check valve prevented backflow of blood to the blood bag. A control valve on the plasma-depleted blood collection line was adjusted during the treatment to control blood side pressures and transmembrane pressure difference.

The conditions and results of this example are in Table 1.

TABLE 1

| Elapsed Time | Pulsations per min. (combined) | Blood Flow Rate | Peak Pressure Blood | | Low Pressure Blood | | Plasma Flow Rate | Hct. | Flux |
|---|---|---|---|---|---|---|---|---|---|
| | | | Inlet | Outlet | Inlet | Outlet | | | |
| 6.0 | 60 | 32.67 | 2.5(17.2) | 1.3(9.0) | −2.0(−13.8) | .4(2.8) | 10.61 | 56.2 | .0254 |
| 10.5 | 60 | 23.82 | 2.9(20.0) | 2.0(13.8) | −1.9(−13.1) | .8(5.5) | 8.88 | 60.6 | .0212 |
| 15.0 | 60 | 15.95 | 3.3(22.8) | 2.6(17.9) | −1.5(−10.3) | 1.2(8.3) | 6.26 | 62.5 | .0150 |
| 24.0 | 60 | 16.02 | 2.9(20.0) | 2.4(16.5) | −1.4(−9.7) | 1.0(6.9) | 6.45 | 63.6 | .0154 |
| 27.5 | 65 | 17.43 | 3.1(21.4) | 2.5(17.2) | −1.3(−9.0) | 1.1(7.6) | 6.93 | 63.1 | .0166 |
| 33.5 | 65 | 13.29 | 3.5(24.1) | 2.9(20.0) | −1.1(−7.6) | 1.4(9.7) | 5.49 | 64.7 | .0131 |
| 39.5 | 75 | 13.82 | 3.8(26.2) | 3.3(22.8) | −.9(−6.2) | 1.6(11.0) | 5.62 | 64.0 | .0134 |
| 45.5 | 100 | 17.07 | 4.8(33.1) | 4.1(28.3) | −.1(−.7) | 2.2(15.2) | 6.62 | 62.0 | .0158 |
| 53.0 | 100 | 7.57 | 5.7(39.3) | 5.0(34.5) | .8(5.5) | 3.0(20.7) | 3.80 | 76.3 | .0091 |
| 59.5 | 60 | 20.54 | 4.4(30.3) | 3.7(25.5) | −.4(−2.8) | 1.8(12.4) | 6.62 | 56.0 | .0158 |

No hemolysis was observed during the first 39.5 minutes. Hemolysis was observed during the period when the frequency of pulsations was increased to 100 as a result, it is believed, of the high frequency and the high peak transmembrane pressure difference. After the pump speed and pressure were reduced, the plasma began to clear, indicating that hemolysis had ceased or was lessening.

the low plasma side pressure was about 0 to 0.3 psi (0 to 2.1 kPa) at the center and periphery.

No hemolysis was observed. The conditions and results of this example are in Table 2.

TABLE 2

| Elapsed Time | Blood Flow Rate | Peak pressures Blood | | Low pressures Blood | | Plasma Flow Rate | Hct. | Flux |
| --- | --- | --- | --- | --- | --- | --- | --- | --- |
| | | Inlet | Outlet | Inlet | Outlet | | | |
| 16 | 6.73 | 3.5(24.1) | 3.5(24.1) | .1(.7) | .4(2.8) | 1.98 | 52.4 | .0158 |
| 19 | 6.14 | 3.9(26.9) | 3.8(26.2) | .1(.7) | .6(4.1) | 2.59 | 63.9 | .0207 |
| 28 | 2.13 | 4.2(29.0) | 4.3(29.6) | .1(.7) | 1.0(6.9) | 1.01 | 70.3 | .0080 |
| 32 | 8.44 | 3.4(23.4) | 3.4(23.4) | 0(0) | .2(1.4) | 1.51 | 45.0 | .0120 |
| 38 | 4.24 | 3.8(26.2) | 3.9(26.9) | 0(0) | .5(3.5) | 1.77 | 63.5 | .0141 |
| 44 | 5.40 | 3.7(25.5) | — | 0(0) | — | 1.68 | 53.7 | .0134 |

EXAMPLE 2

This example illustrates plasmapheresis by reciprocatory pulsatile filtration as per the invention using a single membrane.

The membrane was supported by a polyethylene plate (120 μm pores). The flow path surface area was about 0.013 m². The depth of the flow path was about 6 mils (152 μm) from the center thereof to a point along its radius about 3.25" (8.3 cm) therefrom, from which point, the depth tapered to about 9 mils (229 μm) at the end of the flow path. The peripheral edge of the membrane was pressed between the discs. Blood flowed radially across the first surface of the membrane while plasma which passed through the membrane passed through the pores in the polyethylene plate and flowed radially in a plasma flow region cut into the inside surface of the plasma-side disc.

Reciprocatory pulsatility and reductions in transmembrane pressure difference were provided by a peristaltic rotary pump which was modified by removal of all but one of the rollers therein. The circular path of the roller was about 5.38" (13.65 cm) of which the roller occluded the tubing for about 5.25" (13.34 cm); the tubing was 0.13" (0.32 cm) ID silicon tubing. Therefore, the displacement of the pump, which was set at 60 rpm, was about 1.1 mL.

A check valve and plasma-depleted blood control valve were used.

The peak plasma side pressure remained at about 1.0 psi (6.9 kPa) at the center and periphery of the module;

EXAMPLE 3.

This example illustrates that reciprocatory pulsatile flow during plasmapheresis can result in an improved rate of plasma separation per unit area of membrane as compared to pulsatile flow without reciprocatory pulsations.

The membrane filter module was the same as in Example 2 except that the entire flow path depth was about 6 mils (152 μm) in depth and the porous plate had pores which were about 70 μm in diameter.

Initially, blood was conducted forward by a pressure infuser cuff wrapped around the blood bag. A 0.5" (1.3 cm) ID control valve positioned between the bag and the module was opened and closed at various intervals (reported in seconds) to generate pulsatile flow. After some time, the infuser cuff was removed and the rotary pump described above in Example 2 was utilized. Then the rotary pump was disconnected and the infuser cuff system was restored.

The conditions and results of this example are in Table 3.

TABLE 3

| Elapsed Time | Pump | Blood Flow Rate | Peak Pressure | | Low Pressure | | Plasma Flow Rate | Hct. | Flux |
| --- | --- | --- | --- | --- | --- | --- | --- | --- | --- |
| | | | Blood Inlet | Plasma Outlet | Blood Inlet | Plasma Outlet | | | |
| 25 | infuser open: 30 closed: 15 | 7.65 | 3.8(26.2) | .1(.7) | .3(2.1) | −.3(−2.1) | .78 | 42.6 | .0062 |
| 36 | infuser open: 20 closed: 25 | 4.34 | 3.7(25.5) | .2(1.4) | .3(2.1) | −.3(−2.1) | .42 | 47.0 | .0033 |
| 41 | rotary | 10.40 | 4.3(29.6) | .1(.7) | .3(2.1) | −.9(−6.2) | 2.62 | 50.7 | .0209 |
| 45 | " | 6.20 | 4.2(29.0) | .4(2.8) | .4(2.8) | −.6(−4.1) | 2.20 | 58.9 | .0176 |
| 55 | infuser open: 4 closed: 12 | 3.65 | 3.4(23.4) | .4(2.8) | .6(4.1) | −.2(−1.4) | .40 | 42.6 | .0032 |
| 62 | infuser open: 4 closed: 12 | 3.44 | 3.3(22.8) | — | .5(3.4) | — | .40 | 43.0 | .0032 |
| 69 | infuser open: 10 closed: 12 | 3.79 | 3.2(22.1) | — | .5(3.4) | — | .45 | 43.0 | .0036 |
| 74 | infuser open: 20 closed: 20 | 3.23 | 3.1(21.4) | — | .2(1.4) | — | .44 | 43.9 | .0035 |

Hemolysis was observed to result when pulsations were generated by the infuser cuff/valve system but not when reciprocatory pulsations were generated by the rotary pump.

EXAMPLE 4

In this example, modules substantially as illustrated in FIGS. 1 and 2 were employed. The membranes were 7 inches (178 mm) in diameter, and provided a total membrane surface area of about 0.05 m². The membranes were adhered to circular plates, made from Du Pont Lucite ® acrylic resin, with General Electric RTV 102 silicon adhesive which had a break elongation of 400%, a tensile strength of 350 psi (2.4 MPa), and a Shore A hardness of 30. The adhesive was applied by hand in a layer about 3 mils (76 82 m) thick.

The same adhesive was used to form blood side supports by placing dots of the adhesive, between the membranes in two concentric circles. The blood flow path between the membranes was about 8 mils (0.20 mm) deep. The adhesive supports were cured on the blood side surface of one membrane at 60° C. overnight prior to assembly of the module. The plates were held together with clamps, without O-rings.

The blood was conducted forward by a 3-arm rotary peristaltic pump. A 0.33 psi (2.3×10³ Pa) check valve was located between this pump and the blood reservoir.

Reciprocatory pulsations and pressure fluctuations were provided by a modified peristaltic pump, positioned on a loop, i.e., a length of tubing, which extended from two peripherally located ports and one centrally located port. The pump was modified so that a single roller, in constant contact with the tubing, oscillated in about a 50 mm stroke at about 40 cycles-min$^{-1}$, thereby displacing about 1.6 mL per stroke. A micrometer control valve was placed on the plasma-depleted blood outlet line and was adjusted during the treatment.

Results and conditions of this treatment are summarized in Table 4. No hemolysis was observed.

EXAMPLE 5

The apparatus used in this example was identical to that described above in Example 4 except that the module was smaller, the membranes being about 6 inches (152 mm) in diameter and providing a total membrane surface area of about 0.04 m².

Results and conditions of this treatment are summarized in Table 5. No hemolysis was observed.

TABLE 5

| Elapsed Time (min) | Blood Inlet Flow Rate (mls.-min.$^{-1}$) | Blood Flow Path Pressure | | | | Plasma Flow Rate (mls.-min.$^{-1}$) | Outlet Hct. | Flux |
|---|---|---|---|---|---|---|---|---|
| | | Peak | | Low | | | | |
| | | Inlet | Outlet | Inlet | Outlet | | | |
| 3.0 | 22.1 | 2.0(13.8) | .7(4.8) | −1.2(8.3) | −.8(5.5) | 9.4 | 66.2 | .024 |
| 7.0 | 23.4 | 3.0(20.7) | 2.0(13.8) | −.3(2.1) | 0(0) | 12.3 | 80.3 | .030 |
| 12.5 | 10.2 | 3.4(23.4) | 2.3(15.9) | −1.0(6.9) | −.2(1.4) | 5.7 | 86.6 | .014 |
| 17.0 | 25.4 | 3.3(22.8) | 2.5(17.2) | .3(2.1) | .5(3.4) | 13.0 | 77.9 | .032 |
| 20.5 | 25.2 | 4.4(30.3) | 3.9(26.9) | 1.9(13.1) | 2.2(15.2) | 12.8 | 76.2 | .032 |

EXAMPLE 6

The apparatus used in this example was substantially identical to that described in Example 5. The stroke length of the oscillating pump was varied during the treatment. The oscillator was turned off for a three minute interval so that, during this period, blood was being conducted forward only. The inlet hematocrit was 37%.

Results and conditions of this treatment are summarized in Table 6. Slight hemolysis was briefly observed when the stroke length was changed from four inches (101 mm) to three inches (76 mm) and again when the oscillator was turned on after the one minute interval of constant flow.

TABLE 6

| Elapsed Time (min) | Oscillator Stroke Length (mm) | Blood Inlet Flow Rate (mls.-min.$^{-1}$) | Blood Flow Path Pressure | | | | Plasma Flow Rate (mls.-min.$^{-1}$) | Outlet Hct. | Flux |
|---|---|---|---|---|---|---|---|---|---|
| | | | Peak | | Low | | | | |
| | | | Inlet | Outlet | Inlet | Outlet | | | |
| 1 | 101 | 51.3 | 3.2(22.1) | 1.2(8.3) | — | −1.0(6.9) | 13.9 | 50.7 | .035 |
| 3.5 | 76 | 53.5 | 2.5(17.2) | .7(4.8) | −1.0(6.9) | −.4(2.8) | 14.7 | 51.0 | .037 |
| 7.0 | 76 | 53.8 | 2.9(20.0) | 1.8(12.4) | .1(.7) | .3(2.1) | 18.1 | 55.7 | .045 |
| 9.0 | 76 | 53.4 | 4.0(27.6) | 3.5(24.1) | 2.1(14.5) | 2.1(14.5) | 17.9 | 55.6 | .045 |
| 10.0 | 0 | 53.7 | 3.5(24.1) | 3.5(24.1) | 3.4(23.4) | 3.4(23.4) | 3.8 | 38.8 | .010 |
| 13.0 | 76 | 52.9 | 2.3(15.9) | 1.5(10.3) | .3(2.1) | .5(3.4) | 9.8 | 45.3 | .025 |
| 16.0 | 51 | 54.1 | 3.2(22.1) | 2.6(17.9) | 1.7(11.7) | 1.7(11.7) | 16.4 | 53.0 | .041 |

BEST MODE

The best mode for carrying out the invention is illustrated generally by Examples 4 and 5.

UTILITY

The process and apparatus of the invention have several useful applications including the treatment of certain disease states by plasma exchange or plasma

TABLE 4

| Elapsed Time (min) | Blood Inlet Flow Rate (mls.-min.$^{-1}$) | Blood Flow Path Pressure | | | | Plasma Flow Rate (mls.-min.$^{-1}$) | Outlet Hct. | Flux |
|---|---|---|---|---|---|---|---|---|
| | | Peak | | Low | | | | |
| | | Inlet | Outlet | Inlet | Outlet | | | |
| 3.0 | 23.7 | 1.5(10.3) | .6(4.1) | −.8(5.5) | −.6(4.1) | 8.6 | 59.5 | .017 |
| 8.5 | 14.1 | 2.2(15.2) | 2.0(13.8) | −.4(2.8) | −.1(.7) | 8.2 | 90.1 | .016 |
| 12.5 | 15.7 | 3.0(20.7) | 3.0(20.7) | .5(3.4) | .3(2.1) | 8.8 | 86.3 | .018 |
| 17.0 | 15.4 | 3.0(20.7) | 2.9(20.0) | .8(5.5) | .6(4.1) | 8.2 | 81.1 | .016 |
| 22.0 | 14.6 | 2.7(18.6) | 2.8(19.3) | .6(4.1) | .7(4.8) | 8.4 | 88.9 | .017 |
| 25.5 | 15.1 | 3.6(24.8) | 3.7(25.5) | 1.9(13.1) | 1.8(12.4) | 8.5 | 86.6 | .017 | therapy, the collection of plasma for various transfusion needs, for further fractionation to isolate specific serum proteins, and for the production of cell culture media. The invention is particularly useful for continuous plasmapheresis.

I claim:

1. Improved method for plasmapheresis wherein whole blood is introduced and conducted in a forward direction from an upstream area of a first surface of each of one or more membranes having cell-retaining pores to a downstream area of the first surface, plasma-depleted blood is collected from the downstream area of the first surface, and plasma is separately collected from a second surface of each of the one or more membranes, in a system closed off from the atmosphere, comprising:
   (a) while maintaining a net positive transmembrane pressure difference across said one or more membranes, conducting plasma-depleted blood in the reverse direction over the first surface by delivering collected plasma-depleted blood to the downstream area of the first surface and reducing the transmembrane pressure difference across said one or more membranes in the upstream area whereat whole blood is introduced to about ≦0 by either withdrawing and collecting blood from the upstream area of the first surface or increasing the pressure on a second surface of the one or more membranes, while collecting blood from the upstream area of the first surface, so that blood in the upstream area of the first surface is at a pressure which is lower than the downstream plasma-depleted blood pressure;
   (b) terminating the reverse conducting of step (a);
   (c) while maintaining the net positive transmembrane pressure difference across the membrane, conducting whole blood in the forward direction over the first surface by delivering collected blood from step (a) to the upstream area of the first surface and reducing the transmembrane pressure difference across said one or more membranes in the downstream area whereat plasma-depleted blood is collected to about ≦0 by either withdrawing and collecting plasma-depleted blood from the downstream area of the first surface or increasing the pressure on a second surface of the one or more membranes, while collecting plasma-depleted blood from the downstream area of the first surface, so that plasma-depleted blood in the downstream area of the first surface is at a pressure which is lower than the upstream blood pressure;
   (d) repeating steps (a) to (c) in sequence; and
   (e) collecting plasma at a rate of at least about 0.01 mL/min/cm$^2$ of membrane and plasma-depleted blood having a hematocrit of at least about 60%.

2. Method of claim 1 wherein the transmembrane pressure difference is reduced to below zero.

3. Method of claim 1 which comprises conducting the blood forward and reverse at a velocity up to about 400 mm-sec$^{-1}$.

4. Method of claim 1 wherein the transmembrane pressure difference is reduced from a peak of about 1.5 psi (10 kPa) to below zero.

5. Method of claim 4 in which blood is conducted forward and reverse across each of one or more planar membrandes in flow paths having a height of about 4 to 10 mils (102 to 254 μm) at a pulsation frequency of about 40 to 80 pulsations per minute and at a velocity up to about 450 mm-sec$^{-1}$.

6. Method of claim 5 in which blood is conducted over membranes having cell retaining pores, 0.4 to 0.5 μm in average diameter, having elongation of less than about 65%, modulus of at least about 10 kpsi (70 MPa) and tensile strength of at least about 3000 psi (20 MPa), when tested wet, and being supported on plasma sides.

7. Method of claim 5 in which blood is conducted from the centers of each of a plurality of circular membranes having cell retaining pores, 0.1 to 1.0 μm in average diameter, and being supported on plasma sides.

8. Method of claim 7 in which the transmembrane pressure difference is reduced to about −0.8 to −1.0 psi (−5.3 to −6.9 kPa).

9. Method of claim 7 in which blood is conducted over smooth capillary pore membranes having cell retaining pores, 0.4 to 0.5 μm in average diameter, having elongation of less than about 65%, modulus of at least about 3000 psi (20 MPa), when tested wet, and being supported on plasma sides.

10. Method of claim 9 in which blood is conducted between two membranes.

11. Method of claim 10 in which the membranes are supported on both sides, each plasma side support comprising a fabric-like material.

12. Method of claim 11 in which each plasma side support comprises a plurality of layers of a nonwoven polyester fabric.

13. Method of claim 12 in which there is an elastomeric seal between each membrane and each plate and the blood side support comprises a plurality of smooth pillars.

14. Improved plasmapheresis apparatus comprising one or more membranes having cell-retaining pores, means for conducting blood through a blood flow path forward at a net positive transmembrane pressure difference and reverse over a first surface of each membrane, means for reducing the transmembrane pressure difference during the forward and reverse conducting of blood, means for collecting plasma which passes through each membrane from a second surface thereof, means for withdrawing and collecting blood from each said first surface, means for withdrawing and collecting plasma-depleted blood from each said first surface, means for delivering collected blood to each said first surface, means for delivering collected plasma-depleted blood to each said first surface and means for operating the apparatus closed off from the atomosphere.

15. Apparatus of claim 14 wherein the means for conducting blood over the first surface of each membrane include means for reducing the transmembrane pressure difference to below zero.

16. Apparatus of claim 14 which comprises means for conducting the blood forward and reverse at a velocity up to about 400 mm-sec$^{-1}$.

17. Apparatus of claim 14 wherein the means for conducting blood over the first surface of each membrane include means for reducing the transmembrane pressure difference from a peak of about 1.5 psi (10 kPa) to below zero.

18. Apparatus of claim 17 comprising one or more planar membranes having cell retaining pores, means defining flow paths having a height of about 4 to 10 mils (102 to 254 μm) and means for conducting the blood forward and reverse at a frequency of about 40 to 80 pulsations per minute and a velocity up to about 250 mm-sec$^{-1}$.

19. Apparatus of claim 18 wherein said one or more planar membranes comprise membranes having cell-retaining pores, 0.4 to 0.5 μm in average diameter, having elongation of less than about 65%, modulus of at least about 10 kpsi (70 MPa) and tensile strength of at least about 3000 psi (20 MPa), when tested wet, which are supported on the plasma sides.

20. Apparatus of claim 18 wherein said one or more planar membranes comprise a plurality of circular membranes having cell-retaining pores, 0.1 to 1.0 μm in average diameter, which are supported on the plasma sides and means for conducting blood from the centers of the membranes.

21. Apparatus of claim 20 which includes means for reducing the transmembrane pressure difference to about −0.8 to −1.0 psi (−5.3 to −6.9 kPa).

22. Apparatus of claim 20 wherein said one or more planar membranes comprise thin, smooth capillary pore membranes having cell-retaining pores, 0.4 to 0.5 μm in average diameter, having elongation of less than about 65%, modulus of at least about 10 kpsi (70 MPa) and tensile strength of at least about 3000 psi (20 MPa), when tested wet, which are supported on the plasma sides.

23. Apparatus of claim 22 having the blood flow path 2 between two membranes.

24. Apparatus of claim 23 in which the membranes are supported on both sides and each plasma side support comprises a fabric-like material.

25. Apparatus of claim 24 in which each plasma side support comprises a plurality of layers of a nonwoven polyester fabric.

26. Improved apparatus including a plasmapheresis membrane filter module comprising:
first and second opposing module housing plates having circular recesses within opposing surfaces so as to form a blood flow region between two plasma flow regions; said plates defining a central blood inlet port connected to the blood flow region, a plasma depleted blood outlet port, a blood collection channel, around the blood flow region, connected to said plasma-depleted blood outlet port, a plasma output port and a plasma collection channel around each plasma flow region connected to said plasma outlet port;
a plasma-side support within each plasma flow region;
a pair of membranes, having cell-retaining pores, between each plasma flow region and the blood flow region, there being an elastomeric seal between each membrane and each plate and a blood flow path between the membranes;
means for conducting blood forward at a net positive transmembrane pressure difference and reverse over a first surface of each membrane;
means for reducing the transmembrane pressure difference during the forward and reverse conducting of blood;
means for collecting plasma which passes through each membrane from a second surface thereof;
means for withdrawing and collecting blood from the blood flow region;
means for delivering collected blood to the blood flow region;
means for withdrawing and collecting plasma-depleted blood from the blood flow region;
means for delivering plasma-depleted blood to the blood flow region; and
means for operating the apparatus closed off from the atmosphere.

27. The apparatus of claim 26 in which the depth of the blood flow region between the membranes is at least about 4 mils (102 μm) and the seal is an elastomeric adhesive.

28. The apparatus of claim 27 in which the depth of the blood flow path between the membranes is about 4 to 10 mils (102 to 254 μm).

29. The apparatus of claim 28 in which the membranes are comprised of polyester or polycarbonate and are less than about 1 mil (25 μm) thick.

30. The apparatus of claim 29 in which the membranes are less than about 0.5 mil (13 μm) thick and the adhesive has a break elongation of at least about 100%.

31. The apparatus of claim 29 in which the adhesive has a break elongation of about 400%.

32. The apparatus of claim 29 in which the membranes provide an effective surface area of about 0.02 to 0.06 m² and have cell-retaining pores of about 0.1 to 1.0 μm in averge diameter.

33. The apparatus of claim 29 in which blood side supports comprised of a plurality of smooth pillars are located between the membranes.

34. The apparatus of claim 33 in which the plasma side supports are comprised of layers of fabric-like materials.

35. The apparatus of claim 34 in which the membranes have a total effective surface area of about 0.02 to 0.06 m² and the cell-retaining pores are about 0.4 to 0.5 μm in average diameter.

36. The apparatus of claim 35 having blood side supports between the membranes which supports comprise substantially circular dots of an elastomeric adhesive.

* * * * *